United States Patent [19]
Wu

[11] Patent Number: 5,040,523
[45] Date of Patent: Aug. 20, 1991

[54] STRUCTURE OF PHYSICAL TRACTION MACHINE

[75] Inventor: Kuang-Hsing Wu, Hsin Tien, Taiwan

[73] Assignee: Jaeger Industrial Co., Ltd., Hsin Tien, Taiwan

[21] Appl. No.: 571,237

[22] Filed: Aug. 23, 1990

[51] Int. Cl.[5] .......................... A61F 5/00; A61F 5/01; A61F 5/04

[52] U.S. Cl. ........................................ 128/75; 128/78; 128/84 R; 128/76 R

[58] Field of Search ............... 128/75, 78, 84 R, 84 C, 128/85, 87 R, 87 B, 76 R

[56] References Cited

U.S. PATENT DOCUMENTS

| | | | |
|---|---|---|---|
| 1,356,365 | 10/1920 | Hosmer | 128/75 |
| 3,662,750 | 5/1972 | Jorgensen | 128/75 |
| 4,114,611 | 9/1978 | Lyle et al. | 128/75 |

FOREIGN PATENT DOCUMENTS

| | | | |
|---|---|---|---|
| 3420858 | 12/1985 | Fed. Rep. of Germany | 128/75 |
| 1084049 | 1/1955 | France | 128/84 R |
| 170623 | 6/1965 | U.S.S.R. | 128/84 |

*Primary Examiner*—Richard J. Apley
*Assistant Examiner*—Karen G. Horowitz
*Attorney, Agent, or Firm*—Fleit, Jacobson, Cohn, Price, Holman & Stern

[57] ABSTRACT

A physical traction machine has two U-shaped brackets connected in parallel with a telescopic rod vertically attached thereto at the middle for carrying a traction device to pull a patient's neck or waist for relieving pressure from cervical vertebrae or lumbar vertebrae. An adjusting device is attached to the first U-shaped bracket for adjusting its width. Another adjusting device is attached to the second U-shaped bracket for adjusting its height.

4 Claims, 5 Drawing Sheets

STRUCTURE OF PHYSICAL TRACTION MACHINE

BACKGROUND OF THE INVENTION

1. Field of the Invention

The present invention is related to physical traction machines, and more particularly to a physical traction machine for pulling the neck and the waist for relieving pressure from cervical vertebrae and lumbar vertebrae.

2. Prior Art

In medical science, there are seven methods commonly accepted by physicians for treating ankylosing spondylitis, herniated discs, nerve root compression, sciatica and vertebral arthritis, which include (a) lying in bed; (b) pelvic traction; (c) spinal brace; (d) physical therapy; (e) trunk bending exercises; (f) surgery; and (g) medicinal treatment. Each of the above-said methods has its own disadvantanges, and traction treatment is considered to be an important method for treating osteopathia. The conventional physical traction machines are generally designed for a specific purpose, i.e. each of them is specifically designed for pulling a specific part of the body. For example, a roller type of waist traction machine is specifically designed for securing to a professional work table for pulling the waist so as to help relieve pressure from lumbar vertebrae, and a neck traction machine is specifically designed for pulling the neck so as to help relieve pressure from cervical vertebrae. Therefore, it is apparent that one common disadvantage of the conventional traction machines is their limited application (single purpose application). Another disadvantage of the conventional traction machines is the expensive manufacturing cost, since said traction machines always need to be used with another apparatus, such as a professional use table. A yet further disadvantage of the conventional traction machines is that, according to statistic information those who need to use traction machines are mostly old people who have difficulty in movement, and it is very inconvenient for those patients to go to the hospital for continuous long term treatment. Besides that, those patients also need someone to help them operate a traction machine, i.e. help them to put on or take off the standard weights thereon.

SUMMARY OF THE INVENTION

It is one object of the present invention to provide a physical traction machine which can be alternatively used to pull the neck as well as the waist for relieving pressure from cervical vertebrae and lumbar vertebrae.

Another object of the present invention is to provide a physical traction machine which can be conveniently operated by a patient without any help from others.

Still another object of the present invention is to provide a physical traction machine which can be conveniently adjusted to fit patient's body size.

A yet further object of the present invention is to provide a physical traction machine which is simple in structure and inexpensive to manufacture.

To achieve the above objects and according to the present invention, a physical traction machine comprises a pair of U-shaped brackets connected in parallel by a connecting rod at the middle. A telescopic rod is attached to the connecting rod, which has a daughter rod member driven by a hand-wheel through a guide screw to carry a hanging device located at the top of the daughter rod. When the neck or the waist of a patient is suspended from the hanging device, the traction movement controlled through the hand-wheel will cause a pull strength to the neck or the waist for relieving pressure from cervical vertebrae or lumbar vertebrae. The strength can be adjusted from 0 to 200 Lbs. Through adjusting the device attached to the first U-shaped bracket and another device attached to the second U-shaped bracket, the width and the height can be adjusted to the level to fit the patient's body size.

BRIEF DESCRIPTION OF THE DRAWINGS:

The present invention will now be described by way of example, with reference to the annexed drawings, in which.

Figure 1:
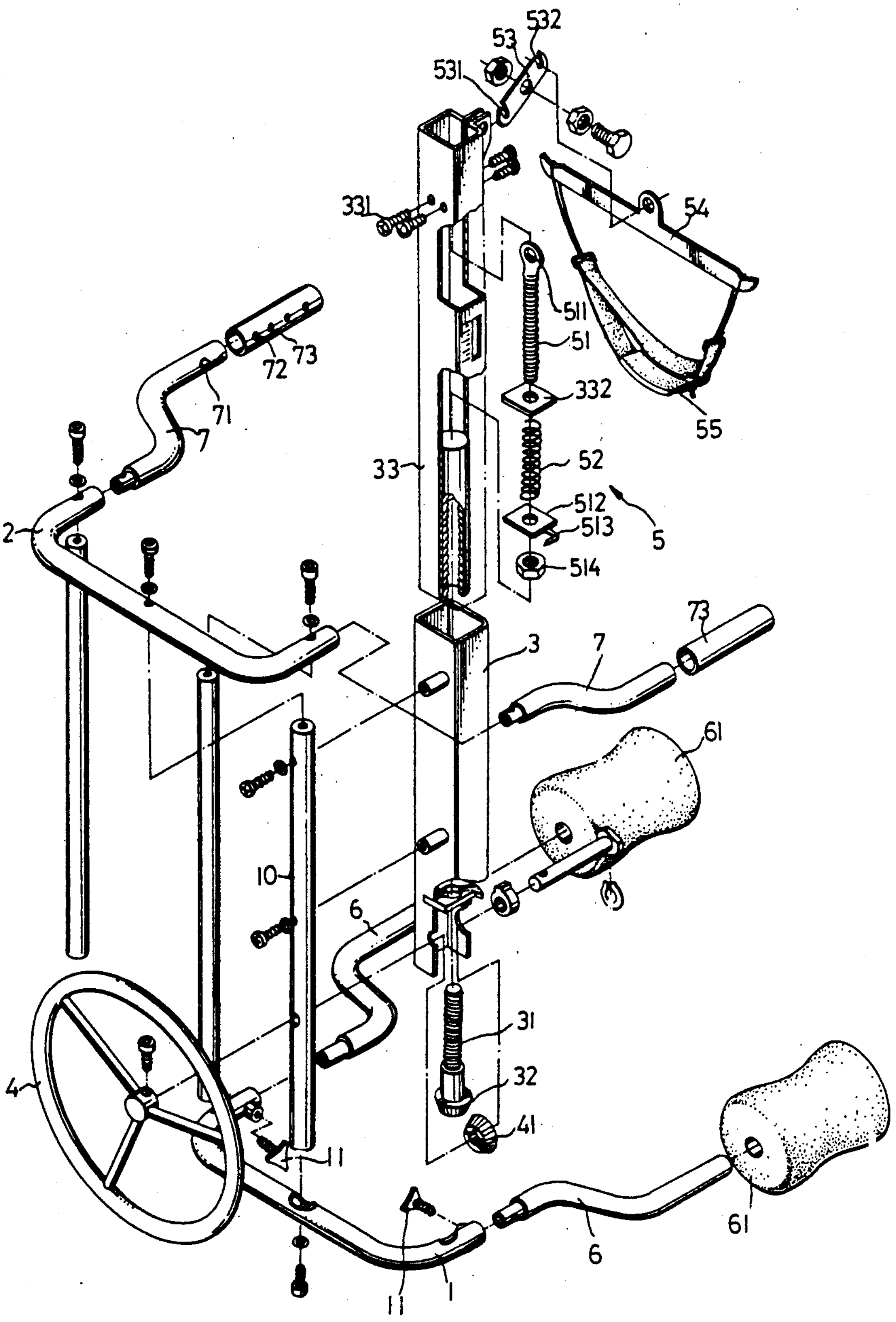
FIG. 1 is a perspective dismantled view of the preferred embodiment of the present invention.
Figure 2:
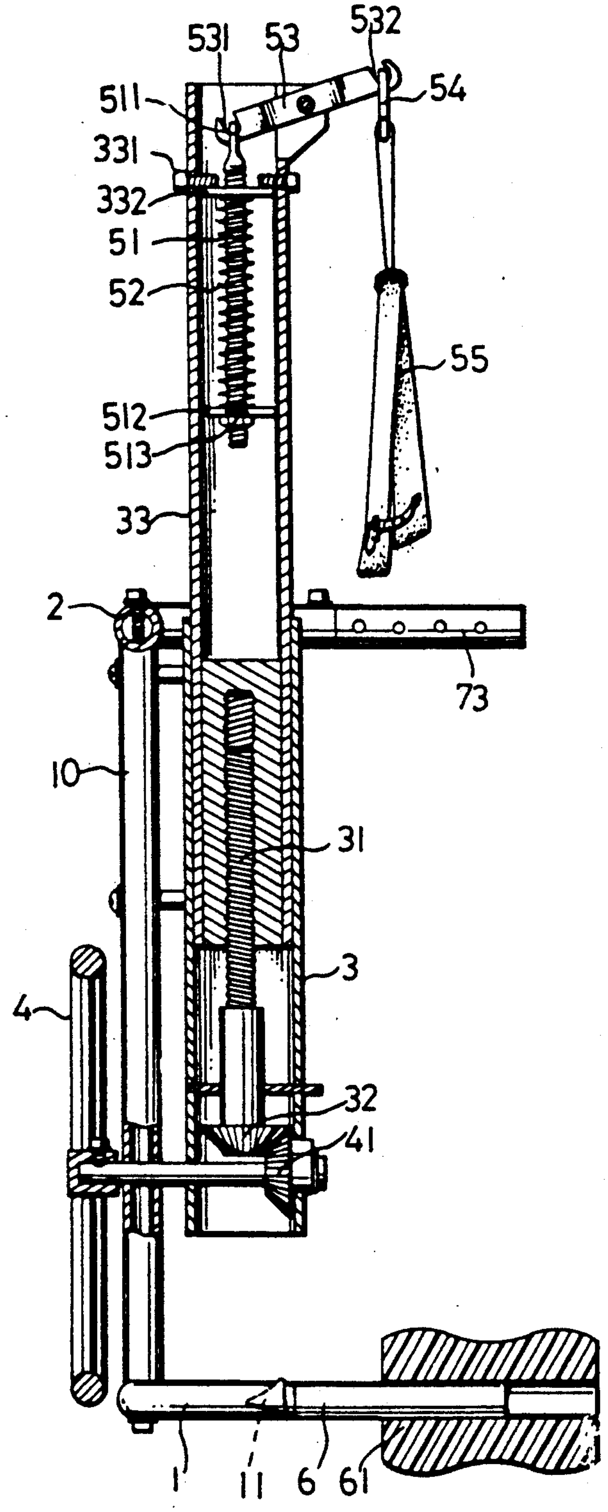
FIG. 2 is a sectional assembly view thereof.

DETAILED DESCRIPTION OF THE PREFERRED EMBODIMENT:

Turning now to the annexed drawings in greater detail and referring first to FIG. 1, a physical traction machine in accordance with the present invention comprises two U-shaped support brackets 1,2, connected in parallel by a connecting rod 10 at the middle of the brackets. There is a telescopic rod 3 attached to the connecting rod 10, which has a daughter rod member 33 controlled to slide therein by a guide screw 31 which has a bevel gear 32 attached thereto at one end and engaged with a bevel gear 41 at the bottom end of a hand-wheel 4. Therefore, the daughter rod member 33 can be controlled to slide in and out of the mother rod member 3 by means of rotating the hand-wheel 4. There is a traction device 5 attached to the daughter rod member 33 at the front end, which is comprised of a screw rod 51, a compression spring 52, a hook member 53, a hanging rod 54, and a retainer 55. The screw rod 51 has an unitary eyed head 511 at the top and a stop plate 512 attached thereto at a lower end by a nut 514. The screw rod 51 is inserted inside the daughter rod member 33 with its stop plate 512 stopped by a locating plate 332 which is fixedly fastened in the daughter rod member 33 by screws 331. Therefore, the screw rod 51 is allowed to move in and out of the daughter rod member 33 and is stopped by the locating plate 332 from. The compression spring 52 becoming detached sleeved on the screw rod 51 between the locating plate 332 and the stop plate 512 is to provide the screw rod 51 with spring force (see FIG. 2). The hook member 53 is pivoted to the daughter rod member 33, having at one end a first hooked portion 531 hooked up with the eyed head 511 of the screw rod 51 and at an opposite end a second hooked portion 532 hooked up with the hanging rod 54 which is further coupled with the retainer 55. After the retainer 55 is mounted on the distressed part of the body, the hand-wheel 4 is rotated to drive the daughter rod member 33 of the telescopic rod 3 to slide in and out so as to drive the traction device 5 to pull the distressing part of the body for physical therapy. There is a degree of resilience in the traction device due to the spring mounting of rod 51.

Figure 3:
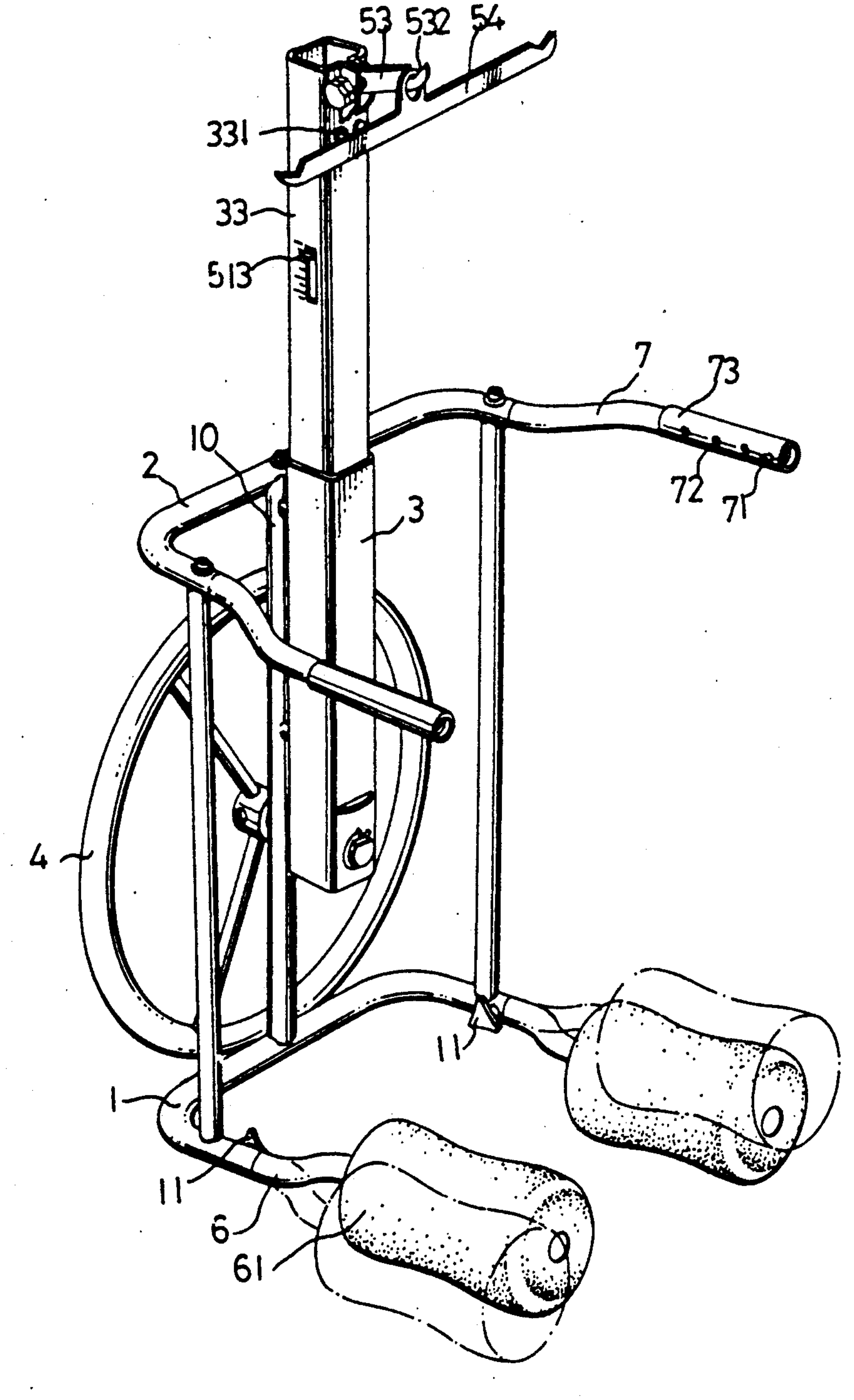
FIG. 3 and is a perspective view of the device and illustrates an operation adjusting the width adjusting rod assembly.

Referring to FIG. 3, there is a width adjusting rod assembly 6 attached to the bottom of the first U-shaped bracket 1 for adjusting the width of the first U-shaped bracket 1. The width adjusting rod assembly 6 comprises two curved rods having each an end fastened in either end of the U-shaped bracket 1 and an opposite end fastened in a socket 61. By means of rotating the width adjusting rod assembly 6, the width of the first U-shaped bracket 1 can be adjusted to fit the size of the chest by rotation of the curved rods. After adjusting, the width adjusting rod assembly 6 is is fixedly secured in position in the first U-shaped bracket 1 by screws 11.

Figure 4:
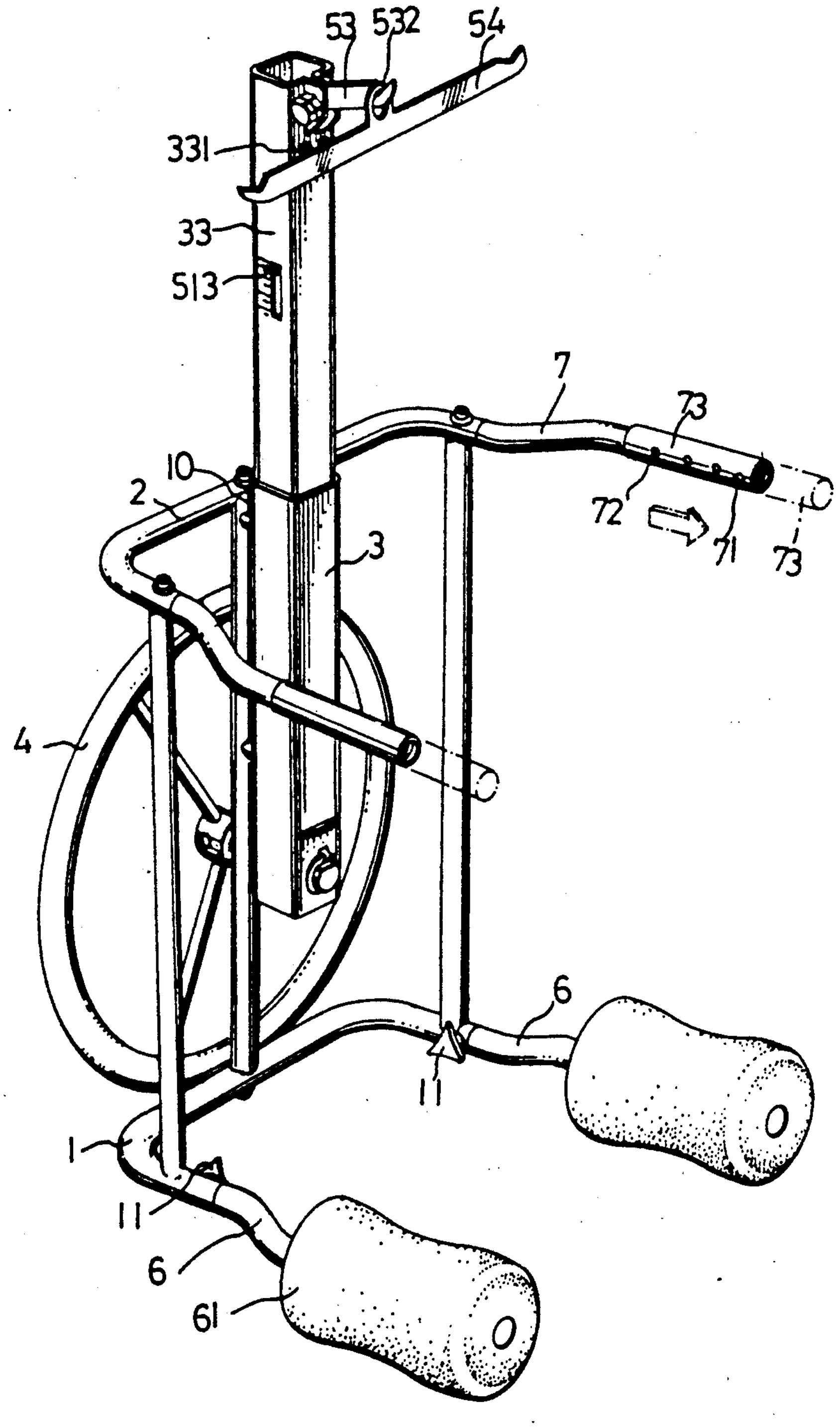
FIG. 4 is a perspective view of the device and illustrates an operation in adjusting the height adjusting rod assembly.

Referring to FIG. 4, there is a height adjusting rod assembly 7 attached to the bottom of the second U-shaped bracket 2 for adjusting the height of the second U-shaped bracket 2 and the angle of inclination of the traction device relative to the first U-shaped bracket 1. The height adjusting rod assembly 7 comprises two curved rods 7 having each an end fixedly fastened in either end of the second U-shaped bracket 2 and an opposite end releasably fastened in a tube 73 with a side pin 71 set in either of the plurality of holes 72 on such a tube 73 for positioning.

Figure 5:
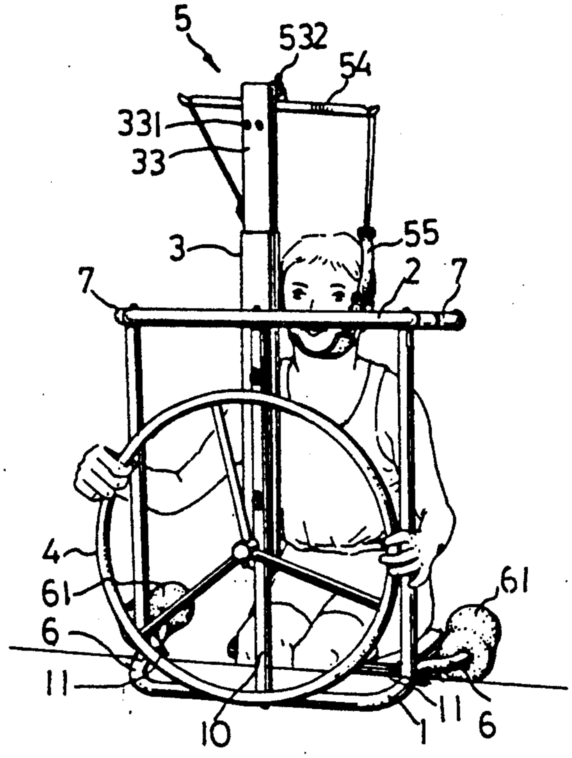
FIG. 5 illustrates the operation of the present invention in pulling the neck.

FIG. 5 illustrates the operation of the present invention in pulling the neck for relieving pressure from cervical vertebrae. The machine is placed in vertical position with the first U-shaped bracket 1 disposed at the bottom, the telescopic rod 3 vertically disposed upward and the traction device 5 disposed at the top. After the retainer 55 is mounted on the neck of a patient who sits behind the machine, a patient can rotate the hand-wheel 4 to drive the daughter rod member 33 to carry the traction device 5 to pull the neck for relieving pressure from cervical vertebrae.

Figure 6:
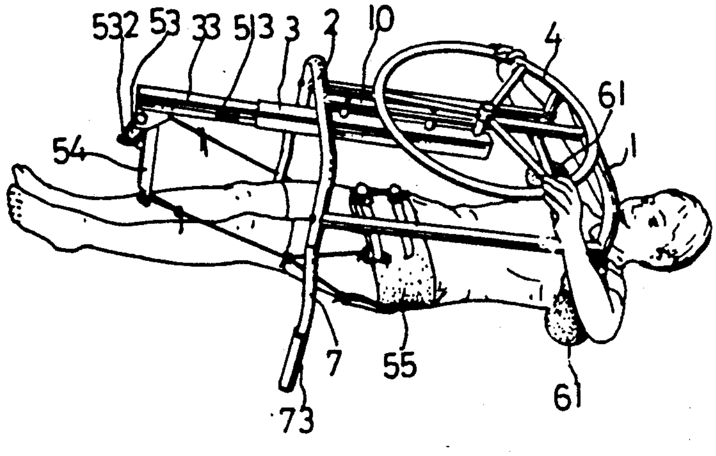
FIG. 6 illustrates the operation of the present invention in pulling the waist.

FIG. 6 illustrates the operation of the present invention in pulling the waist for relieving pressure from lumbar vertebrae. The machine is placed in horizontal position and the patient lies on the ground beneath the two U-shaped brackets 1, 2 with the feet resting by the traction device 5 and with the retainer 55 mounted on the waist. Before operation, the width adjusting rod assembly 6 must be properly adjusted so that the two sockets 61 are comfortably respectively retained in the armpit, and the height adjusting rod assembly 7 shall also be properly adjusted so that the waist is properly lifted by the retainer 55 from the ground for the a certain range. Thus, the patient can rotate the hand-wheel 4 by hand to drive the traction device 5 to pull the waist so as to relieve pressure from lumbar vertebrae.

Further, there is a pointer 513 attached to the stop plate 512 extending out of the daughter rod member 33 at one side where a scale is printed for indication of tractive effort.

I claim:

1. A physical traction machine, comprising:

a first U-shaped bracket connected with a second U-shaped bracket in parallel and in spaced apart planes;

a substantially tubular telescopic rod vertically attached to said U-shaped brackets at the center of the U-shape and having one end of a tubular daughter rod member controlled to slide therein by a guide screw;

a hand-wheel having a gear engaged with said guide screw to drive said daughter rod member to slide in said telescopic rod;

a width adjusting rod assembly attached to said first U-shaped bracket at the free ends thereof for adjusting the width of said first U-shaped bracket;

a height adjusting rod assembly rod assembly attached to said second U-shaped bracket at the free ends thereof for adjusting the height of said second U-shaped bracket;

a traction device movably fastened in the other end of said daughter rod member;

a hanging device at the other end of said daugther rod member for securing said traction device to a patient's neck or waist; and characterized in that said hand-wheel can be rotated to carry said daughter rod member to slide in said telescopic rod so as to drive said traction device to pull the neck or .waist of a patient through said hanging device for relieving pressure from cervical vertebrae or lumbar vertebrae.

2. The physical traction machine of claim 1, wherein said traction device comprises a screw rod mounted for lengthwise movement in the daughter rod member, the screw rod having an unitary eyed head at an upper end thereof and a stop attached thereto at a lower end, said stop plate being adapted to engage a locating plate fastened inside said daughter rod member to prevent removal of the screw rod from the daughter rod member, a compression spring sleeved on said screw rod between said locating plate and said stop plate, a hook member pivoted to said daughter rod member at said one end, said hook member having at one end a first hooked portion hooked up with said eyed head and at an opposite end a second hooked portion hooked up with said hanging device, and a pointer attached to said stop plate and extending out of said daughter rod member at one side for indication of tractive effort, the machine including a scale on the outer wall of said daughter rod member for cooperating with the pointer.

3. The physical traction machine of claim 1, wherein said width adjusting rod assembly comprises two curved rods each having one end rotatably fastened in a respective end of said first U-shaped bracket and an opposite end fastened in a socket said curved rods being rotatable for adjusting the width of said first U-shaped bracket and screws in the first U-shaped bracket whereby said curved rods can be fixedly secured in a desired position relative to said first U-shaped bracket.

4. The phsyical traction machine of claim 1, wherein said height adjusting rod assembly comprises two curved rods each having one end fastened in a respective end of said second U-shaped bracket and an opposite end releasably fastened in a tube, said opposite end having a side pin releasably set in one of a line of holes on said tube for positioning the tube on the respective curved rod in a selected position.

* * * * *